(12) United States Patent
Redel et al.

(10) Patent No.: US 7,650,179 B2
(45) Date of Patent: Jan. 19, 2010

(54) COMPUTERIZED WORKFLOW METHOD FOR STENT PLANNING AND STENTING PROCEDURE

(75) Inventors: Thomas Redel, Poxdorf (DE); Estelle Camus, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 627 days.

(21) Appl. No.: 11/298,772

(22) Filed: Dec. 9, 2005

(65) Prior Publication Data

US 2007/0135707 A1 Jun. 14, 2007

(51) Int. Cl.
*A61B 5/05* (2006.01)
(52) U.S. Cl. .................. 600/427; 623/1.1; 623/1.13; 623/1.12; 623/1.11; 623/3.3
(58) Field of Classification Search .............. None
See application file for complete search history.

(56) References Cited

U.S. PATENT DOCUMENTS

| | | | |
|---|---|---|---|
| 5,830,145 A | | 11/1998 | Tenhoff |
| 6,293,966 B1 * | | 9/2001 | Frantzen ............ 623/1.15 |
| 2001/0031920 A1 * | | 10/2001 | Kaufman et al. ........ 600/431 |
| 2004/0097805 A1 * | | 5/2004 | Verard et al. .......... 600/428 |

FOREIGN PATENT DOCUMENTS

WO WO 97/32182 9/1997

OTHER PUBLICATIONS

Slager et al (True 3 dimensional reconstruction of coronary arteries in patients by fusion of angigraphy and IVUS and its quantitative validation), American heart association, published in 2000.*

True 3-Dimensional Reconstruction of Coronary Arteries in Patients by Fusion of Angiography and IVUS (ANGUS) and Its Quantitative Validation, Slager et al., Circulation, vol. 102 (2000) pp. 511-516.

Brochure for AXIOM Artis and Interventional Cardiac 3D (C13D), Siemens Medical (Feb. 2005).

* cited by examiner

*Primary Examiner*—Long V Le
*Assistant Examiner*—Joel F Brutus
(74) *Attorney, Agent, or Firm*—Schiff Hardin LLP

(57) ABSTRACT

In a computerized workflow method for stent planning and conducting a stenting procedure, characteristics of a lesion to be stented are determined from a 3D planning image of the region and selection of an actual stent for stenting the lesion is made with computer-assisted analysis of the lesion based on the characteristics. A virtual stent is electronically generated based on the actual stent, and, using the virtual stent, a best position for the actual stent, for effectively stenting the lesion, is determined. A real time 2D image of the lesion-containing region is displayed during the stenting procedure, with the virtual stent included therein at the aforementioned best position. A physician manually guides the actual stent relative to the lesion during the stenting procedure until the position of the actual stent, as seen in the displayed real time 2D image, coincides with the virtual stent in that image.

20 Claims, 3 Drawing Sheets

COMPUTERIZED WORKFLOW METHOD FOR STENT PLANNING AND STENTING PROCEDURE

BACKGROUND OF THE INVENTION

1. Field of the Invention

The present invention relates to techniques for planning a stenting procedure, including selection of an appropriate stent, and for conducting the stenting procedure, in which the stent is implanted in a subject at an appropriate location.

2. Description of the Prior Art

The use of percutaneous coronary interventions, particularly stenting procedures, has become the treatment of choice for many manifestations of coronary artery disease.

Stenting procedures also are widely performed to treat stenosis in blood vessels other than the coronary arteries, such as the renal artery or the mesenteric artery, or other peripheral vessels.

Although stenting greatly enhances the patient's quality of life by relieving the patient's symptoms and reducing ischemia almost immediately, this technique has not proven to be completely successful on a long-term basis for many patients. The lack of success in some patients is due to a phenomenon known as restenosis inside or near the stented area. The occurrence of restenosis is often due to a misplacement of the stent, or a sub-optimal choice of the stent type or stent size.

The stent type and size are determined by the physician performing the stenting procedure based on measurements of the size and extent of the lesion area obtained from an angiography x-ray projection (image). Since an angiography x-ray projection is a 2D image, however, and it is being used to measure a 3D structure, a 3D structure that is not substantially completely in the plane of the angiography projection will appear foreshortened in the 2D image.

Moreover, stent placement is performed based on visualization of the stent delivery catheter on a real-time 2D x-ray projection acquired without contrast agent injection. This means that the lesion most likely will not be clearly visible in this real-time 2D x-ray projection, and thus the physician must place the stent somewhat blindly when the physician considers the stent delivery catheter to be correctly placed based on the physician's memory of the vessel anatomy (obtained from a previous x-ray projection using contrast agent injection). Again, foreshortening of 3D objects in the 2D x-ray projection can impair the correct placement of the stent delivery catheter.

To improve the accuracy of such lesion measurements, it is known to generate a 3D reconstruction of the lesion-containing region of the patient based on multiple 2D x-ray projections of the diseased vessel. In such a 3D reconstruction, it is possible to measure the lesion size and extent three-dimensionally, which significantly reduces errors due to the foreshortening effect. As a consequence, selection of the appropriate stent to treat the lesion in question is improved.

Other techniques are known to control the position and expansion of the stent in the diseased vessel. For example, post-processing algorithms are known that enhance the visualization of a stent (particularly the stent struts) in a 2D x-ray projection. Intravascular ultrasound (IVUS) techniques as well as optical techniques such as optical coherence tomograph (OCT) are also known and used to assist in visualizing the stent relative to the vessel wall. These techniques, however, are used post-interventionally (after the stent placement). At this point, the implanted stent cannot be removed and cannot even be shifted to a better location within the vessel. This means that if the stent is not correctly placed in the stenting procedure, a second stent may have to be implanted to better treat the lesion area.

SUMMARY OF THE INVENTION

An object of the present invention is to provide an improved method, with computerized support, for planning a stenting procedure to treat a lumen afflicted with a lesion in the body of a patient, including selection of the most appropriate stent for the procedure, as well as for conducting the stenting procedure itself. It is a further object of the present invention to provide such computerized support for the stenting procedure in real-time.

It is a further object of the present invention to provide such a method wherein some or all of the method steps are completely automated, i.e. once an appropriate input entry has been made, the step proceeds without any further intervention by the physician.

The above object is achieved in accordance with the present invention in a computerized workflow method for stent planning and for conducting a stenting procedure, wherein the stenting procedure is monitored in real-time using a C-arm fluoroscopic imaging system. The method includes the following basic phases. 3D image data are acquired from the region of the subject containing a lesion that is to be treated by stenting, and a 3D of the image is reconstructed from the image data. Analysis of the stenosis associated with the lesion is undertaken using the 3D image, including a determination of the size, lesion length, lesion extent, tissue composition, vessel wall elasticity, etc. The 3D image is then also used for stent planning, including stent selection and simulation of the localization of the selected stent with regard to the lesion, and visualization of the result of placement of the selected stent. Once a satisfactory stent placement is determined, an angulation selection can be made that sets the angle of the C-arm of the fluoroscopy system, and thus the image plane, that is best suited to monitor the actual stenting procedure. The stenting procedure is then conducted with monitoring using the C-arm fluoroscopy system with the C-arm at the selected position.

The stenosis analysis can be conducted with intervention by the physician to identify and mark, on a computer screen, points indicating the aforementioned characteristics of the stenosis. Alternatively, using known pattern recognition and image processing software, the aforementioned characteristics can be automatically determined by the computer in which the stenosis analysis software is running. The results automatically determined by the computer can then be displayed to the physician, who can either accept them, modify them, or make changes in the underlying inputs and re-run the analysis.

The same is true regarding the stent planning including the stent selection. Based on the results of the stenosis analysis, the computer can display a list of available, appropriate stents, from which the physician can make a selection by interaction with the computer. Alternatively, the computer can execute a stent selection program in which a stent is automatically selected based on the results of the stenosis analysis. Simulation of a virtual representation of the selected stent in the 3D image is then undertaken by the computer. Based on a coincidence of certain structural points of the virtual stent with points associated with the lesion in the 3D image, a determination is made as to whether the selected stent is in fact appropriate for treating the lesion in question. This determination can be made either by the physician, upon viewing the virtual representation of the selected stent overlaid on the displayed 3D image, or can be made automatically by the computer, again using suitable pattern recognition and image analysis software. If the physician is not satisfied with the stenting that will be achieved by the selected stent, based on the simulation, the physician can select a different stent and re-run the simulation. Alternatively, the computer can do the same without intervention by the physician, until coincidence, within a predetermined minimum deviation between the virtual simulation of the selected stent and the designated points associated with the lesion in the 3D image is achieved.

The angulation selection for the fluoroscopy C-arm also can be made by the physician, or can be made automatically by the computer.

In the stenting procedure itself, the 2D real-time image of the lesion containing region, acquired with the C-arm fluoroscopy system, can be correlated with the planning image data set (i.e. the previously-acquired 3D image of the lesion-containing region). The optimized deployed position of the virtual representation of the selected stent can be overlaid on the real-time 2D image during the stenting procedure. In the stenting procedure, the actual stent is visualized in the subject in the real-time 2D image, and is manually brought into coincidence with the displayed optimal deployed position of the virtual representation. It is thus assured that the actual stent is placed in the subject at the optimal position and location that were determined using the simulation.

DESCRIPTION OF THE PREFERRED EMBODIMENTS

Figure 1:
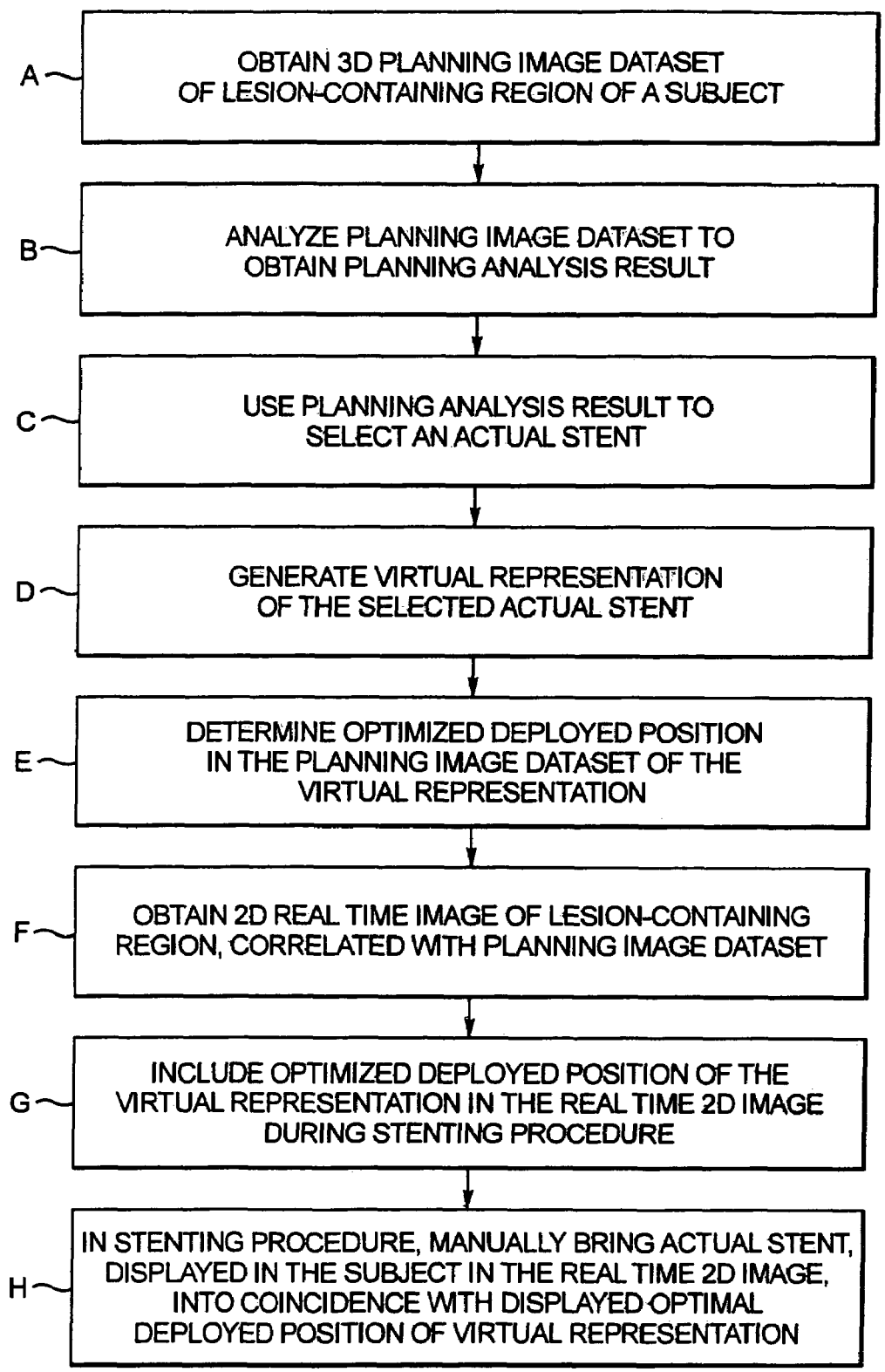
FIG. 1 is a flow chart including basic steps in the computerized planning and execution of a stenting procedure in accordance with the invention.

Certain basic steps in the inventive method are shown in the flow chart in FIG. 1, for computerized planning of a stenting procedure and computerized assistance in conducting the stenting procedure itself.

In step A, a 3D planning image data set is acquired of a lesion-containing region of a subject, and a 3D image is reconstructed from this data set in a known manner. The 3D image data set and image reconstruction can be undertaken using AXIOM Artis and Intervention Cardiac 3D (IC 3D), commercially available from Siemens AG. The data acquisition can be 3D or 4D. In this known data acquisition, an x-ray image of the diseased vessel, with contrast agent injection, is acquired with a C-arm system with the C-arm in a position to acquire the image in a first plane. The C-arm is then moved to a second angle position and the image of the diseased vessel, with contrast agent injection, is obtained in a second plane, different from the first plane. One of these images is then presented at a display and, by user interaction with the displayed image, a physician designates (marks) appropriate points around the lesion in the displayed plane. A 3D or 4D image reconstruction is then undertaken in a known manner based on the image acquisitions acquired in the first and second planes. The reconstructed image (or more precisely, the data set underlying the reconstructed image) includes the designations entered by the physicians. This data set is referred to below as a planning image data set.

In step B, the planning image data set is analyzed to obtain a planning analysis result. This can be undertaken using a vessel analysis and virtual stenting software program at a workstation of the imaging modality that was used to obtain the planning image data set, or can take place at a different location with the planning image data set being made available online at the remote location. The planning image is analyzed (stenosis analysis) to identify appropriate characteristics concerning the lesion to be stented, such as size, length of the lesion, extent of the lesion, tissue composition, vessel wall elasticity, etc. This analysis can be performed by the physician by appropriate interaction with the displayed planning image. Alternatively, the stenosis analysis can be undertaken completely automatically in a computer, using known pattern recognition and image processing software. The result of step B is a set of characteristics that are sufficient to allow an appropriate stent to be selected from among available stents (or at least to allow an initial selection to be made, subject to further refinement).

The selection of an actual stent from among the available stents based on the planning analysis result is made in step C. Again, this can proceed manually, with interaction by the physician, or completely automatically within the computer. In the manual embodiment, the physician selects a stent from a stent data base, which can be a list of stents sorted by stent manufacturer, stent type and stent size. This selection is made based on the set of characteristics obtained in step B. Alternatively, using these same characteristics, an automatic computerized search of the stent data base can be made, according to various selection criteria and search rules.

After the actual stent has been selected, in step D the computer generates a virtual representation of the selected actual stent. In step E, the optimized deployed position of the actual stent is determined by superimposing the virtual representation of the selected actual stent on the planning image data set. Using pattern recognition and image processing software, the computer can identify the best position of the computer model (virtual representation) of the selected stent within the reconstructed image. This analysis takes into account the degree of shrinkage of the stent that can be expected during stent expansion. If the characteristics obtained in the stenosis analysis include information such as tissue composition and/or vessel wall elasticity, this information can also be included in the simulation.

The computer then displays the simulation results by showing the virtual representation of the stent within the displayed planning image. As is conventional, the actual stent will be provided with markers, such as at opposite ends of the stent, that will be visible in the real-time visualization of the stent that is displayed during the stenting procedure. The catheter that is used to introduce the stent also will be provided with at least one such marker. Virtual indications of where these markers should be located, when the stent is placed in the optimal position are included in the simulation result.

In the computerized simulation, it may be the case that the virtual representation of the selected stent does not result in a sufficiently close match with the dimensions and position of the lesion in the planning image. If this is the case, the simulation program can automatically revert to step C, and select a different stent and re-run the simulation, until a stent is found that results in a sufficiently close match (within the programmed optimization criteria) to the lesion in the planning image.

Figure 2:
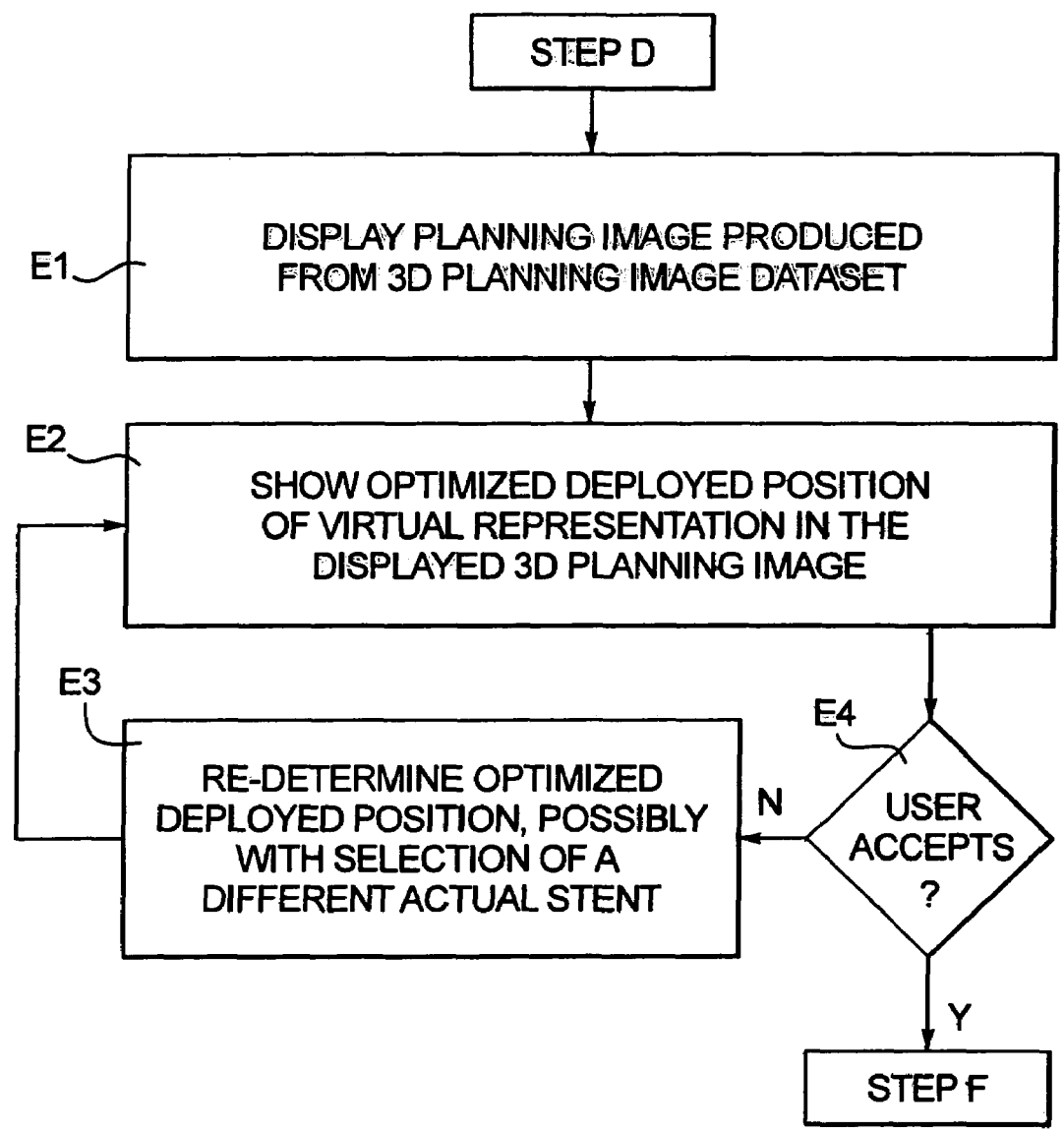
FIG. 2 is a more detailed flow chart for an embodiment of step E in the flow chart of FIG. 1.

As an alternative, at least that portion of step E can be implemented manually, with physician interaction, as shown in FIG. 2. In this manual version of step E, the planning image produced from the 3D planning image data set is displayed in step E1. The optimized deployed position of the virtual representation of the selected stent is displayed for the physician in the 3D planning image in step E2. The physician then has the option of accepting this deployed position, in step E4. If the physician agrees that the displayed deployed position is optimal, the physician makes an appropriate entry via the computer interface, and the method proceeds to step F, explained below. If the physician does not agree that the currently displayed deployed position is optimal, in step E4 the physician declines to accept this proposal, and in step E3 the computer re-determines the optimized deployed position. In this re-determination, the physician can be prompted or permitted to enter modification suggestions that will be taken into account by the computer in the re-determination of the optimized deployed position, or the physician may actually specify a modified position. In this re-determination of the optimized deployed position, it is also possible that the physician or the computer may determine that the currently-selected stent cannot satisfy the optimization criteria, in which case the physician or the computer may select a different actual stent, and a virtual representation of this different selected stent is then generated by the computer for use in the re-determination of the optimized deployed position.

The determination of the optimized deployed position in step E can also include a determination, made either automatically by the computer or entered manually by the physician, of the angulation position for the C-arm of the fluoroscopy system that will be used to generate the real-time image for monitoring the stenting procedure. This angulation position is selected so that the image plane of the fluoroscopic image (a 2D image) is optimized to minimize foreshortening effects.

In step F, a 2D real-time image of the lesion-containing region is obtained with the C-arm fluoroscopy system, with the C-arm at the appropriate angulation position determined in step E. It is also possible to use a biplanar fluoroscopy system, in which the respective planes of only one, or both, of the C-arms can be determined in step E.

The real-time image of the lesion-containing region is correlated with the planning image data set. In step G, the optimized deployed position of the virtual representation of the selected stent is superimposed on the real-time 2D image during the stenting procedure. The stenting procedure is conducted in step H to implant an actual stent corresponding to the selection made in step C, and possibly refined in step E.

Figure 3:
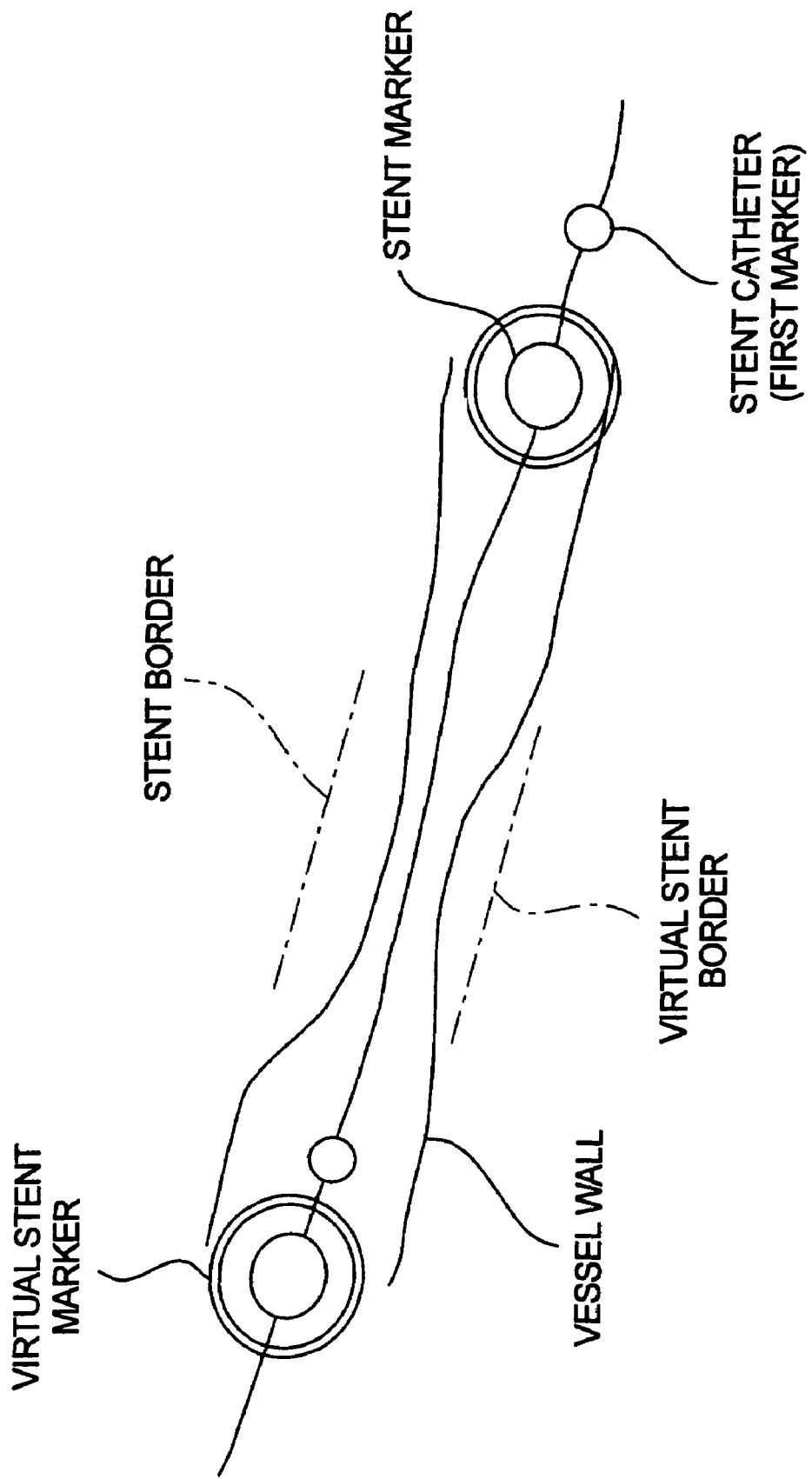
FIG. 3 schematically illustrates a displayed image that is presented to a physician in accordance with the inventive method.

In step H, the virtual representations of the stent markers, as well as a virtual representation of the stent edges (seen as straight lines) are superimposed on the fluoroscopic image or images in real-time during the stent placement procedure. A schematic illustration of such a displayed image is shown in FIG. 3, wherein the constricted vessel wall can be seen from the real-time image, together with the actual stent markers that are visualized in the 2D image, and the marker for the stent catheter, which may be the first marker among a number of stent catheter markers. The virtual stent markers, indicated by double circles in FIG. 3, are superimposed on this 2D fluoroscopic image, together with the virtual stent border. Accurate placement of the actual stent occurs when the respective stent markers are contained within the virtual stent markers. The position of the virtual stent border relative to the vessel wall can also be ascertained from the displayed image when such coincidence of the stent markers with the virtual stent markers exists.

When such alignment and positioning is achieved, the physician triggers deployment of the stent via the catheter, so the stent expands. If the stent border (edge) can be seen in the 2D image, this can be compared with the position of the virtual stent border. As long as the actual stent markers remain within the virtual stent markers, it can be reliably assumed that no dislodgement or displacement of the stent occurred during deployment, and the stent has been deployed in the intended, optimal position.

As the real-time stenting procedure develops, it may occur that the physician may decide that the originally-selected C-arm angulation has become sub-optimal. If so, the physician can change the position of the C-arm of the fluoroscopy system during the stenting procedure to again optimize the presentation of the diseased vessel in the fluoroscopic image. If the angulation is changed, the computer can re-calculate the new positions of the virtual markers and the virtual stent border so that they are accurately shown superimposed in the adjusted fluoroscopic plane.

The planning image (3D planning) image data set can be acquired by 3D image reconstruction using imaging techniques such as IVUS, guided IVUS as described in U.S. Pat. No. 5,830,145, ANGUS as described in "True Three-Dimensional Reconstruction of Coronary Arteries in Patients by Fusion of Angiography and IVUS (ANGUS) and its Quantitative Validation," Slager et al, Circulation 2000, Vol. 102, pages 511-516, or with optical methods such as OCT as described in PCT Application WO97/032182 or OFDI. With such imaging modalities, the planning image includes not only morphological information of the diseased vessel, but also tissue information of the vessel wall. If the planning image is acquired as a 4D data set (i.e., also including a time coordinate) information about the elasticity of the vessel wall can also be included.

A barcode or RFID tag can be used to check that the selected stent (actual stent) has the same specifications as the virtual stent validated by the physician in step C. The computer that will monitor the stenting procedure can be provided with a barcode reader or an RFID detector, the output of which must be approved by the physician in order for the stenting procedure to proceed. If approval is not given, for example, the computer does not proceed to display the virtual stent markers and stent border in the real-time fluoroscopic image.

In step H, when coincidence of the actual stent markers with the virtual stent markers occurs, an audio signal can be emitted, or an optical signal can be provided, such as by causing the virtual stent markers to blink.

As an optional augmentation to the above-described simulation, a fluid dynamics simulation (2D or 3D or 4D) of blood flowing within the virtually stented vessel can be performed, and the results displayed for the physician. The physician then can take this dynamics information into account in deciding whether to approve the simulation results.

The workflow described above can be applied to bifurcated lesions. In such situations, the computer simulation additionally provides a simulation of different stenting techniques (such as stent-in-stent, V-stenting, etc.) so that the physician not only is assisted in selecting the best-suited stent, but also is assisted in selecting the best-suited stenting technique.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computer-assisted stenting, including stent planning, comprising the steps of:

acquiring image data from an internal region of a subject comprising a lumen afflicted with a lesion and reconstructing an at least 3D image of said region from said image data, said 3D image containing and representing characteristics of said lesion;

conducting a stenosis analysis of said lesion characteristics using only said 3D image with at least a portion of said stenosis analysis being automatically electronically conducted by computerized analysis of said lesion characteristics, to obtain a stenosis analysis result;

based on said stenosis analysis result, selecting an actual stent, from among a plurality of available, existing stents of different sizes, to treat said lesion;

in a computer, generating a virtual simulated stent corresponding to said actual stent;

electronically overlaying only said virtual stent on said 3D image and, in a computer, automatically electronically determining a best position of said virtual stent, relative to said lesion, for effectively treating said lesion as well as automatically electronically determining an angulation of a C-arm of an imaging system that will be used during a stenting procedure to implant said actual stent; and conducting said stenting procedure to implant said actual stent, including generating a real time 2D image of said internal region using said imaging system with said C-arm thereof at said angulation, and combining only said virtual stent at said best position in said real time 2D image, and manually guiding said actual stent in said stenting procedure using said real time 2D image to bring said actual stent to an actual position in said internal region coinciding with said best position.

2. A method as claimed in claim 1 wherein the step of reconstructing an at least 3D image of said internal region comprises reconstructing a 4D image of said internal region from said image data.

3. A method as claimed in claim 1 wherein the step of acquiring said image data comprises acquiring image data from said internal region using a biplane or a monoplane C-arm imaging system.

4. A method as claimed in claim 3 wherein the step of acquiring said image data using a biplane or a monoplane C-arm imaging system comprises:

injecting contrast agent into said internal region and acquiring first image data from said internal region in a first plane with said C-arm in a first angulation position; and with said contrast agent in said internal region, acquiring second image data from said internal region in a second plane with said C-arm in a second angulation position;

and wherein the step of reconstructing an at least 3D image from said image data comprises:

reconstructing a first 2D image of said internal region from said first image data set and reconstructing a second 2D image of said internal region from said second image data set, and displaying each of said first and second 2D images;

in each of the displayed first and second 2D images, manually indicating marks delimiting said lesion to indicate a lesion-containing portion in each of said first and second 2D images; and reconstructing said at least 3D image of said region from the respective lesion-containing portions of said first and second 2D images.

5. A method as claimed in claim 1 wherein the step of conducting said stenosis analysis comprises conducting said stenosis analysis completely automatically electronically in a computer, with no manual intervention after starting said stenosis analysis.

6. A method as claimed in claim 1 wherein the step of conducting said stenosis analysis comprises automatically electronically determining at least one intermediate stenosis analysis result and making said intermediate stenosis analysis result available at a computer workstation, and allowing manual intervention via said computer workstation to obtain a final stenosis analysis result.

7. A method as claimed in claim 1 comprising selecting said characteristics in said 3D image, used to conduct said stenosis analysis, from the group consisting of size of said lesion, length of said lesion, extent of said lesion, tissue composition of said lumen, and lumen wall elasticity of said lumen.

8. A method as claimed in claim 1 wherein the step of selecting said actual stent comprises making said stenosis analysis result available to a user, and making a manual selection, by said user of said actual step from among a plurality of available actual stents.

9. A method as claimed in claim 1 wherein the step of selecting a stent comprises automatically electronically comparing said stenosis analysis result to respective sets of stored data representing different available actual stents, to obtain a comparison result, and automatically electronically selecting actual stent based on said comparison result.

10. A method as claimed in claim 9 comprising allowing a user to manually accept the automatically electronically selected actual stent at any time before beginning said stenting procedure.

11. A method as claimed in claim 1 wherein said actual stent comprises a stent marker that is visible in said real time 2D image, and wherein the step of simulating said actual stent as a virtual stent comprises including a virtual representation of said stent marker in said virtual stent.

12. A method as claimed in claim 11 comprising, in said stenting procedure, guiding said actual stent to cause said stent marker in said real time 2D image to coincide with said virtual representation of said stent marker in said virtual stent in said real time 2D image.

13. A method as claimed in claim 1 comprising, in said stenting procedure, guiding said actual stent using a catheter, and wherein the step of determining said best position comprises displaying said 3D image with said virtual stent overlaid thereon and including a representation of said catheter, associated with said virtual stent, in the displayed 3D image.

14. A method as claimed in claim 1 wherein the step of determining said best position comprises determining said best position automatically electronically in a computer without manual intervention after starting said determination of said best position.

15. A method as claimed in claim 1 wherein the step of determining said best position comprises automatically electronically determining an intermediate best position in a computer and making said intermediate best position determination available to a user at a computer workstation, and allowing said user, via said computer workstation, to modify said intermediate best position to obtain a final best position.

16. A method as claimed in claim 15 wherein the step of allowing said user to modify said intermediate best position includes allowing said user to select a different actual stent, and comprising, if a different actual stent is selected, automatically electronically simulating said different actual stent to obtain a virtual different stent, and re-determining said intermediate best position with said virtual different stent overlaid on said 3D image.

17. A method as claimed in claim 1 wherein the step of generating said real time 2D image comprises generating a fluoroscopic image using a C-arm fluoroscopy imaging system.

18. A method as claimed in claim 1 comprising automatically emitting a humanly perceptible signal when the position of said actual stent coincides with said best position.

19. A method as claimed in claim 1 comprising allowing a user, during said stenting procedure, to manually change said angulation of said C-arm to a changed angulation, and automatically electronically re-positioning said best position of said virtual stent in said real time 2D image dependent on said changed angulation.

20. A method for computer-assisted stenting and planning of said stenting, comprising the steps of:
   using an imaging modality in a planning step orientation, generating an at least 3D image data set of an internal region of a subject containing a lumen afflicted with a lesion, and an environment around said lesion, at which an actual stent is to be positioned and deployed in a subsequent stenting procedure;
   using a computer supplied only with said 3D image data set, analyzing said region and said environment in said 3D image data set and producing a lesion-characterizing data set representing anatomical and pathological characteristics of said lesion and said environment;
   using said lesion-characterizing data set, selecting said actual stent for said stenting procedure, from among a plurality of available, existing stents of different sizes, said actual stent having a marker detectable by a stenting procedure imaging modality;
   in said computer, generating a virtual stent corresponding to the selected actual stent, including a virtual marker corresponding to said marker of said actual stent, and electronically overlaying only said virtual stent in said 3D image data set at a virtual deployed position optimized to stent said lesion;
   from said 3D image data set overlaid with said virtual stent, determining an imaging orientation of said stenting procedure imaging modality for conducting said stenting procedure;
   conducting said stenting procedure, including orienting said stenting procedure imaging modality to the selected orientation and generating a real time 2D image of said region with said stenting procedure imaging modality; and
   displaying said real time 2D image during said stenting procedure combined only with said virtual stent at said position optimized to stent said lesion, and manually guiding said actual stent relative to said lesion to cause a representation of said actual stent in said real time 2D image to coincide with said virtual stent.

* * * * *